(12) United States Patent
Musco

(10) Patent No.: US 11,696,965 B1
(45) Date of Patent: Jul. 11, 2023

(54) AUTOMATIC AIR CONDITIONER DRAIN SYSTEM STERILIZER

(71) Applicant: Richard G. Musco, Lake Worth, FL (US)

(72) Inventor: Richard G. Musco, Lake Worth, FL (US)

( * ) Notice: Subject to any disclaimer, the term of this patent is extended or adjusted under 35 U.S.C. 154(b) by 0 days.

(21) Appl. No.: 17/962,622

(22) Filed: Oct. 10, 2022

(51) Int. Cl.
  *A61L 2/18* (2006.01)
  *A61L 2/24* (2006.01)
  *F24F 13/22* (2006.01)

(52) U.S. Cl.
  CPC ............ *A61L 2/18* (2013.01); *A61L 2/24* (2013.01); *F24F 13/222* (2013.01); *A61L 2202/14* (2013.01); *A61L 2202/15* (2013.01); *F24F 2013/227* (2013.01); *F24F 2013/228* (2013.01)

(58) Field of Classification Search
  CPC .......... A61L 2/18; A61L 2/24; A61L 2202/14; A61L 2202/220215; F24F 13/222; F24F 2013/22; F24F 2013/228
  See application file for complete search history.

(56) References Cited

U.S. PATENT DOCUMENTS

| | | | |
|---|---|---|---|
| 5,514,344 A * | 5/1996 | D'Agaro | A61L 2/18 137/561 A |
| 5,558,158 A | 9/1996 | Elmore | |
| 5,755,103 A | 9/1998 | Na et al. | |
| 6,487,868 B2 | 12/2002 | Sato et al. | |
| 7,278,272 B2 | 10/2007 | Huston et al. | |
| 7,392,658 B1 * | 7/2008 | Hardy, III | F24F 13/222 137/15.05 |
| 8,057,751 B2 | 11/2011 | Cheong et al. | |
| 9,943,778 B1 | 4/2018 | Gutierrez et al. | |
| 10,139,119 B2 | 11/2018 | Choi et al. | |
| 10,220,220 B2 | 3/2019 | Kim et al. | |
| 10,514,182 B1 * | 12/2019 | Oviedo | C02F 1/686 |
| 10,928,083 B2 | 2/2021 | Park et al. | |
| 2021/0222898 A1 * | 7/2021 | Verish | F24F 13/20 |

FOREIGN PATENT DOCUMENTS

| CN | 212618900 U | * | 2/2021 |
| KR | 102374640 B1 | * | 3/2022 |

OTHER PUBLICATIONS

English translation for KR 102374640 B1 (Year: 2022).*
English translation for CN 212618900 U (Year: 2021).*

* cited by examiner

*Primary Examiner* — Sean E Conley
(74) *Attorney, Agent, or Firm* — Cramer Patent & Design, PLLC; Aaron R. Cramer

(57) ABSTRACT

The automatic air conditioner drain system sanitizer may comprise a pump, a controller, a solution reservoir, and a power source. The automatic air conditioner drain system sanitizer may be configured to dispense a drain clearing solution from the solution reservoir into a drain line of an air conditioning system periodically in order to prevent growth of microorganisms within the drain line. The microorganisms may be referred to as white slime and may comprise bacteria, algae, mold, mildew, fungus, or any combination thereof. As non-limiting examples, the drain clearing solution may be white vinegar, bleach, chlorine tablet dissolved in water, or a liquid drain line clearing product. The quantity of the drain clearing solution dispensed and the dispensing interval may be selected and may vary based upon the drain clearing solution used.

14 Claims, 6 Drawing Sheets

AUTOMATIC AIR CONDITIONER DRAIN SYSTEM STERILIZER

RELATED APPLICATIONS

Not applicable.

FIELD OF THE INVENTION

The presently disclosed subject matter is directed to an automatic air conditioner drain system sanitizer.

BACKGROUND OF THE INVENTION

Mankind's quality of life in recent times has been vastly improved with the introduction of air conditioning. In fact, there are those who say that air conditioning is a more important invention than that of the computer. However, with all of its enjoyed benefits, the practice of producing a negative heat delta is fraught with disadvantages and problems. Perhaps the biggest difficulty is the production of condensate due to the cold surfaces of the air conditioning coil in warm most air. This condensate must then be carried away to a suitable drain point.

Unfortunately, due the damp and warm conditions, and biological matter that exists in the air, the condensate line becomes an ideal environment for the formation of mold and bacteria. In many cases, this mold or "white slime" as it is often called, can completely block the condensate line causing water backup into the air conditioning equipment which can damage equipment, or even cause water leaking and associated water damage into living areas located below the equipment. Accordingly, there exists a need for a means by which blockage of condensate lines by mold buildup can be eliminated. The development of the air conditioner drain line sterilizer fulfills this need.

SUMMARY OF THE INVENTION

The principles of the present invention provide for an automatic air conditioner drain system sanitizer has a pump moving a plurality of drain clearing solution from a pump inlet to a pump outlet, a solution reservoir containing the drain clearing solution—the solution reservoir includes a reservoir lid, a vent, and a solution reservoir tubing coupler, the pump draws the drain clearing solution into the pump from the solution reservoir, a controller controlling the pump and the solution reservoir, and an operator interface having a manual pump power control switch, a power level display, an interval selection control, and a dispense quantity control.

The pump may be an electromechanical pump or a peristaltic pump. The pump may move the drain clearing solution by applying a rotary motion, a reciprocating motion, a linear motion, or a combination thereof by one or more gears, one or more screws, one or more pistons, one or more rollers, one or more shuttle blocks, one or more vanes, one or more diaphragms, one or more plungers, one or more chains, one or more ropes, one or more impellers, or any combination of the preceding.

The pump may draw the drain clearing solution into the pump from the solution reservoir through a plurality of intake tubing that is fluidly coupled to the pump inlet via an intake tubing coupler. The pump may discharge the drain clearing solution through a plurality of discharge tubing that is fluidly coupled to the pump outlet via a discharge tubing coupler. The drain clearing solution may be dispensed through the discharge tubing into the drain line. The drain line may be operable to drain a plurality of condensation from an evaporator. The drain clearing solution may kill a plurality of microorganisms in the drain line to prevent clogging. The discharge tubing may be routed directly into the drain line via a drain line vent. The discharge tubing may be routed into the drain line via a drain line access port that is capped with a cap. The cap may be replaced with a different cap with an aperture to accommodate the discharge tubing. The discharge tubing may be routed into a bottom of the evaporator via an accessory drain port.

The discharge tubing may be routed into a drain pan under the evaporator which is fluidly coupled to the drain line. The controller may be a microcontroller having a computer processor that includes a central processing unit having one or more integrated circuits that determines when to dispense the drain clearing solution, when to energize the pump, when to control the drain clearing solution dispensed, and when to deenergize the pump. The controller may receive one or more inputs from a timer and controls one or more outputs coupled to a motor drive circuit.

The timer may count a plurality of clock ticks in order to track elapsed time. The controller may include a battery pack containing one or more batteries. The automatic air conditioner drain system sanitizer may further comprise a controller enclosure housing for the controller, the pump, the timer, the motor drive circuit, and the input power conditioning circuit. The controller may include a plurality of controller magnets coupled to the rear of the controller enclosure, at least one battery pack magnets coupled to a rear of the battery enclosure, and at least one solution reservoir magnets coupled to a rear of the solution reservoir.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY

Figure 1:
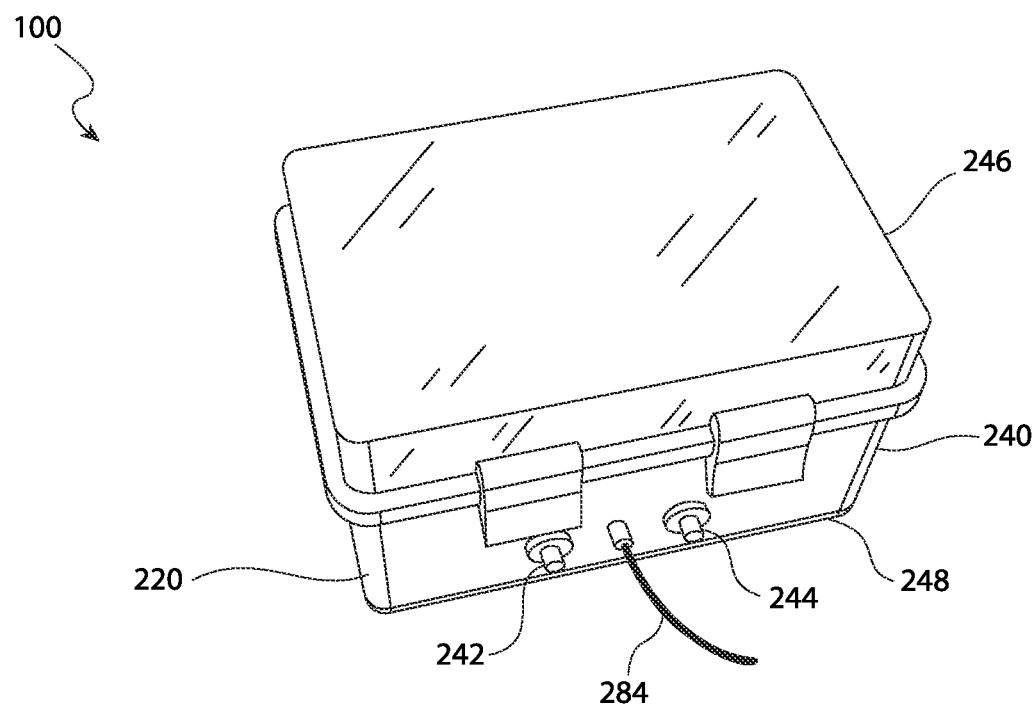
FIG. 1 is a front isometric view of an automatic air conditioner drain system sanitizer, according to an embodiment of the present invention, illustrating the controller with the controller cover closed.
Figure 2:
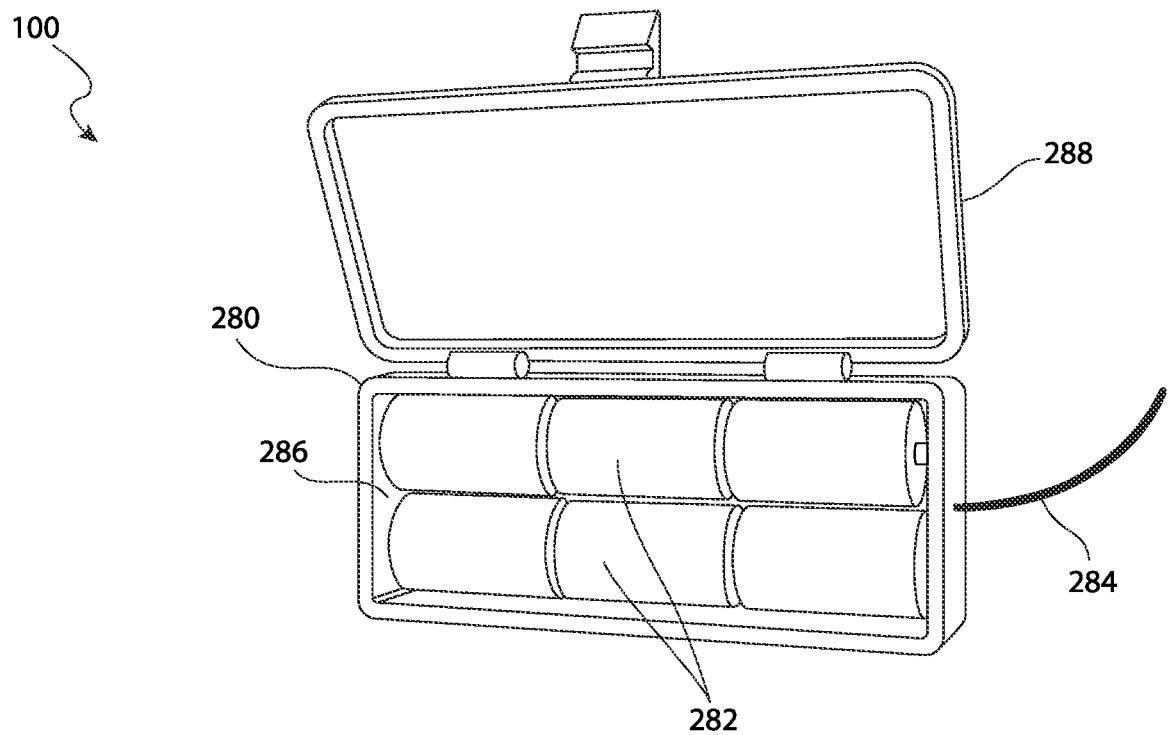
FIG. 2 is a front isometric view of an automatic air conditioner drain system sanitizer, according to an embodiment of the present invention, illustrating the battery pack with the battery pack cover open.
Figure 3:
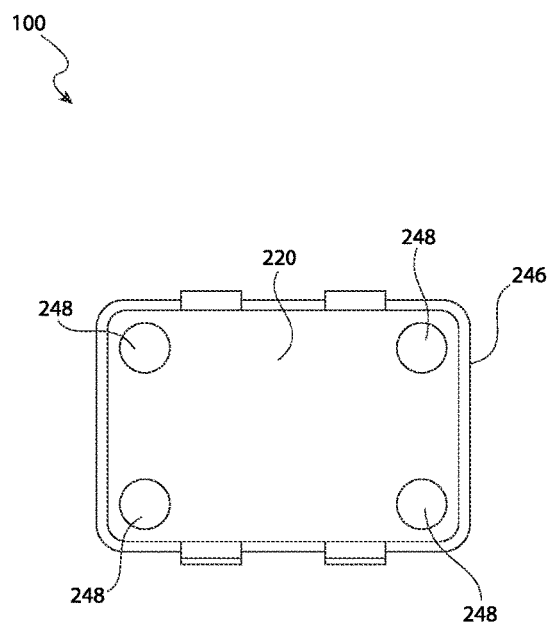
FIG. 3 is a rear view of an automatic air conditioner drain system sanitizer, according to an embodiment of the present invention, illustrating the rear of the controller.
Figure 4:
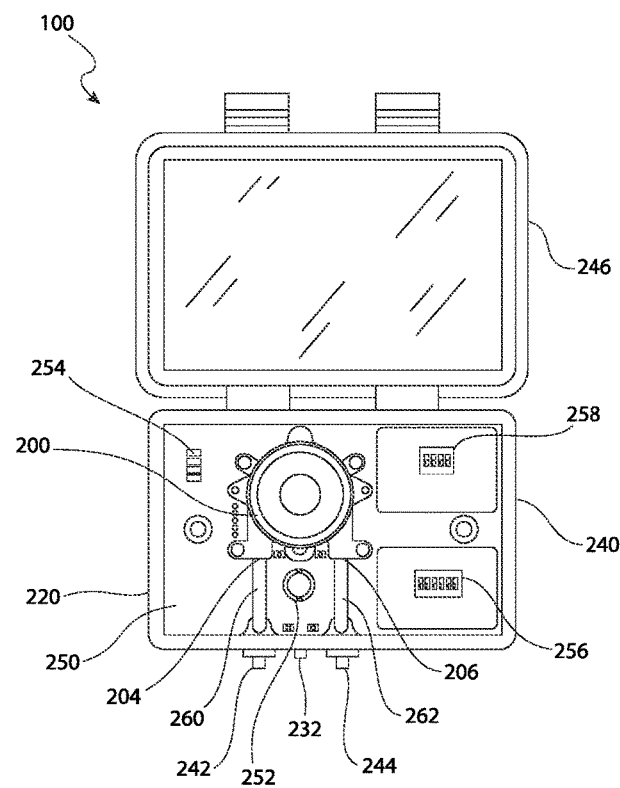
FIG. 4 is a front view of an automatic air conditioner drain system sanitizer, according to an embodiment of the present invention, illustrating the controller with the controller cover open.
Figure 5:
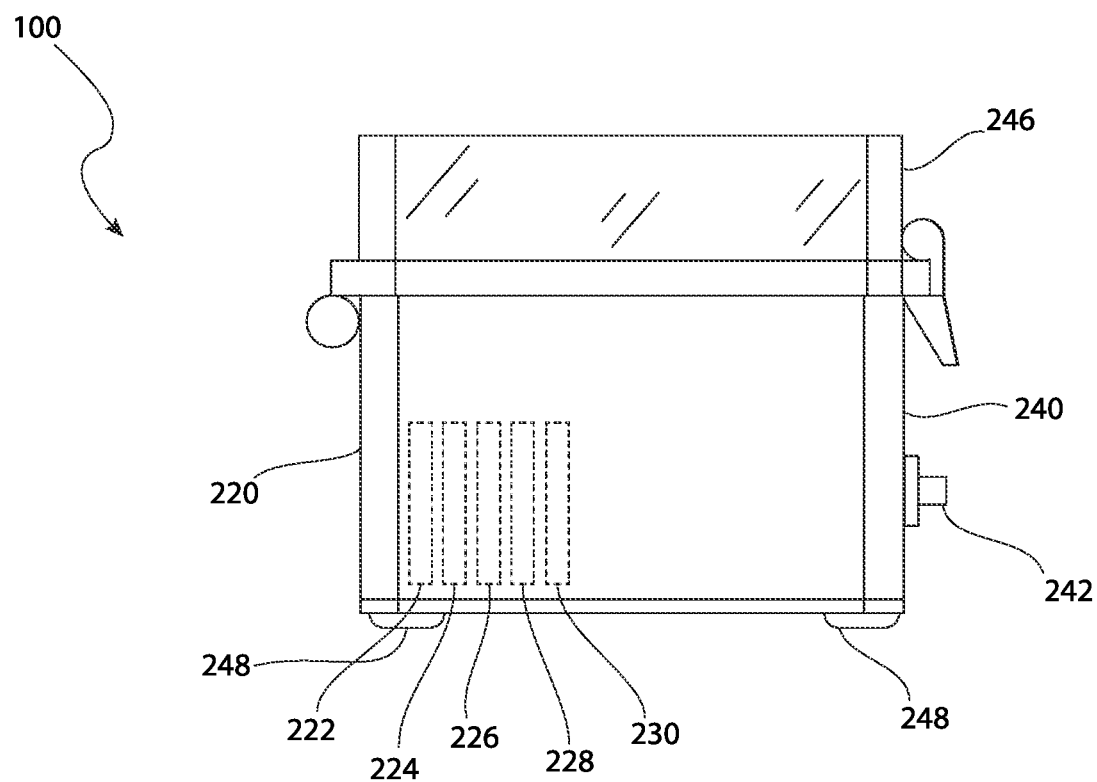
FIG. 5 is a side view of an automatic air conditioner drain system sanitizer, according to an embodiment of the present invention, illustrating the controller with the controller cover closed.
Figure 6:
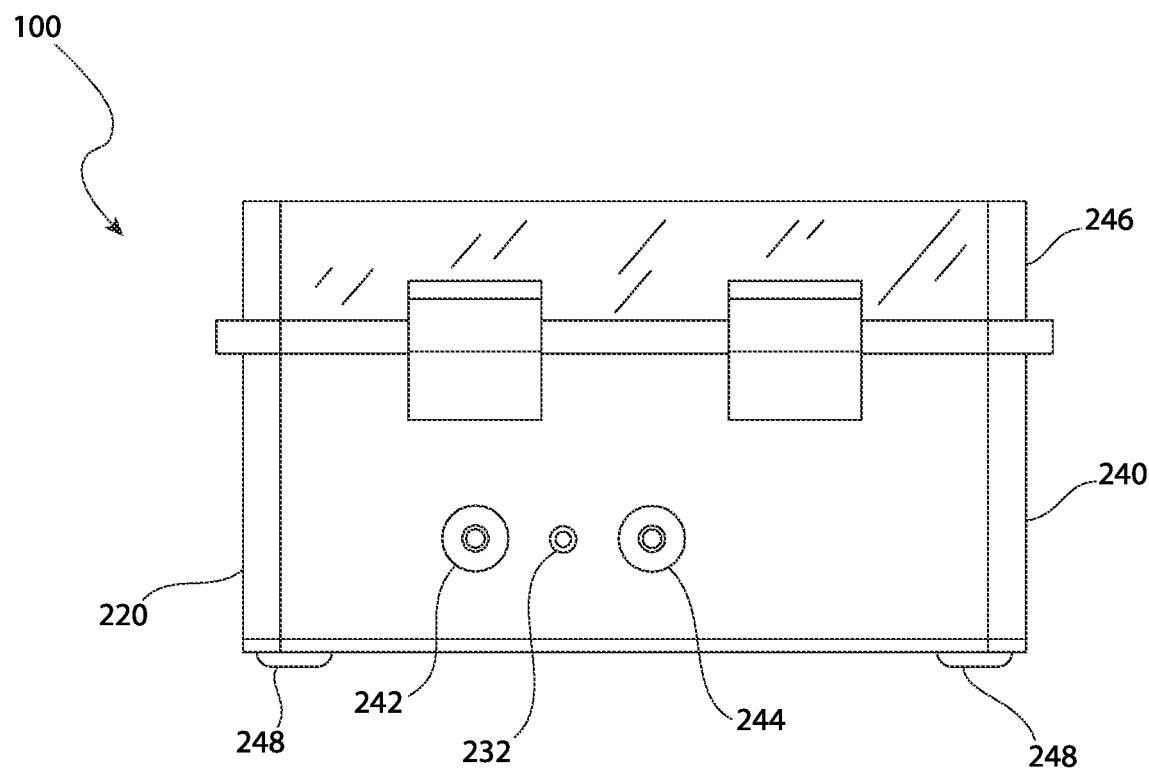
FIG. 6 is a bottom view of an automatic air conditioner drain system sanitizer, according to an embodiment of the present invention, illustrating the controller with the controller cover closed.

- 100 automatic air conditioner drain system sanitizer
- 200 pump
- 204 pump inlet
- 206 pump outlet
- 220 controller
- 222 microcontroller
- 224 timer
- 226 input power conditioning circuit
- 228 supercapacitor
- 230 motor drive circuit
- 232 DC power coupler
- 240 controller enclosure
- 242 intake tubing coupler
- 244 discharge tubing coupler
- 246 controller cover
- 248 controller magnet
- 250 operator interface
- 252 pump control switch
- 254 power level display
- 256 interval selection control
- 258 dispense quantity control
- 260 intake tubing
- 262 discharge tubing
- 270 solution reservoir
- 272 solution reservoir magnet
- 274 reservoir lid
- 276 vent
- 278 solution reservoir tubing coupler
- 280 battery pack
- 282 battery
- 284 DC power cable
- 286 battery enclosure
- 288 battery pack cover
- 290 battery pack magnet
- 292 power adapter
- 900 drain clearing solution
- 912 evaporator pan
- 914 drain line
- 916 drain line vent
- 918 drain pan 1. Description of the Invention The present invention is directed to an automatic air conditioner drain system sanitizer (herein described as the "invention") 100. The invention 100 may comprise a pump 200, a controller 220, a solution reservoir 270, and a power source. The invention 100 may be configured to dispense a drain clearing solution 900 from the solution reservoir 270 into a drain line 914 or pan of the evaporator 912 of an air conditioning system periodically in order to prevent growth of microorganisms within the drain line 914. The microorganisms may be referred to as white slime and may comprise bacteria, algae, mold, mildew, fungus, or any combination thereof. As non-limiting examples, the drain clearing solution 900 may be distilled white vinegar, bleach, chlorine, sanitizing tablets dissolved in water, or a liquid drain line clearing product. The quantity of the drain clearing solution 900 dispensed and the dispensing interval may be selected and may vary based upon the drain clearing solution 900 used. Dispensing one-half to one cup (½-1 c) of the drain clearing solution 900 once a month may be typical.

The pump 200 may move the drain clearing solution 900 from a pump inlet 204 to a pump outlet 206. The pump 200 may be electromechanical and may comprise an internal motor that may be energized by the application of a pump activation signal to the pump 200. As non-limiting examples, the pump 200 may move the drain clearing solution 900 by applying rotary motion, reciprocating motion, linear motion, or a combination thereof to one (1) or more gears, screws, pistons, rollers, shuttle blocks, vanes, diaphragms, plungers, chains, ropes, impellers, or combinations thereof. The pump 200 may draw the drain clearing solution 900 into the pump 200 from the solution reservoir 270 through intake tubing 260 that may be fluidly coupled to the pump inlet 204 via an intake tubing coupler 242. The pump 200 may discharge the drain clearing solution 900 through discharge tubing 262 that may be fluidly coupled to the pump outlet 206 via a discharge tubing coupler 244.

Figure 7:
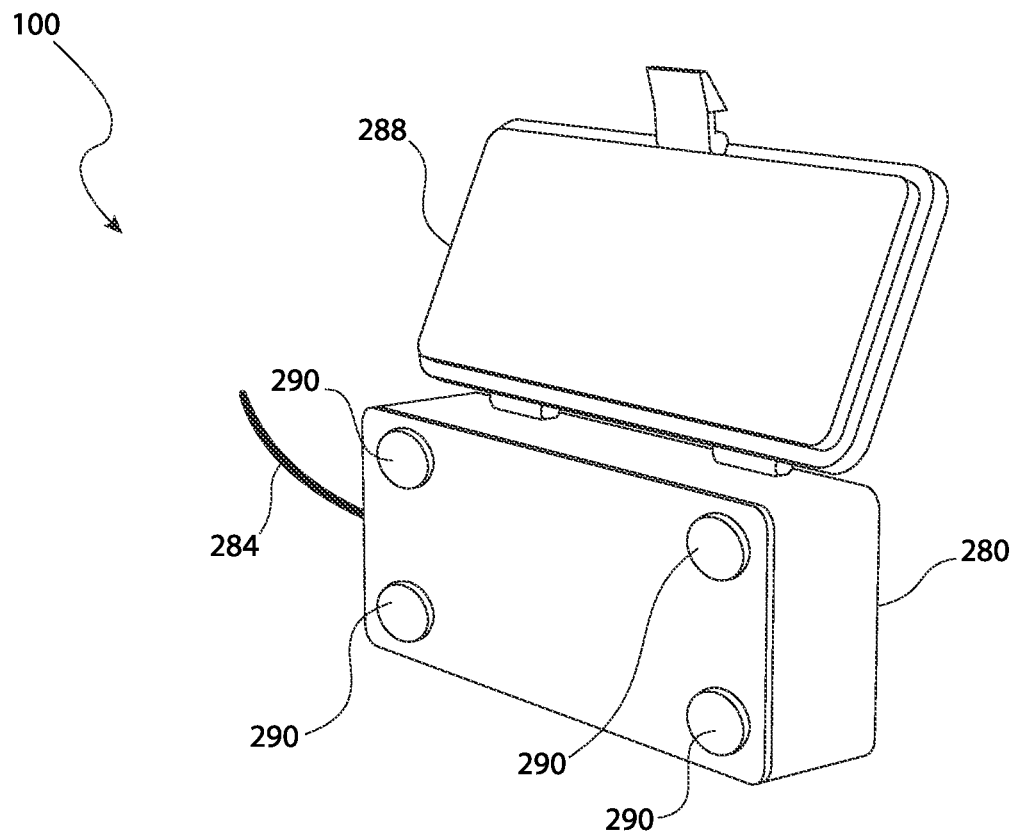
FIG. 7 is a rear isometric view of an automatic air conditioner drain system sanitizer, according to an embodiment of the present invention, illustrating the battery pack with the battery pack cover open.
Figure 8:
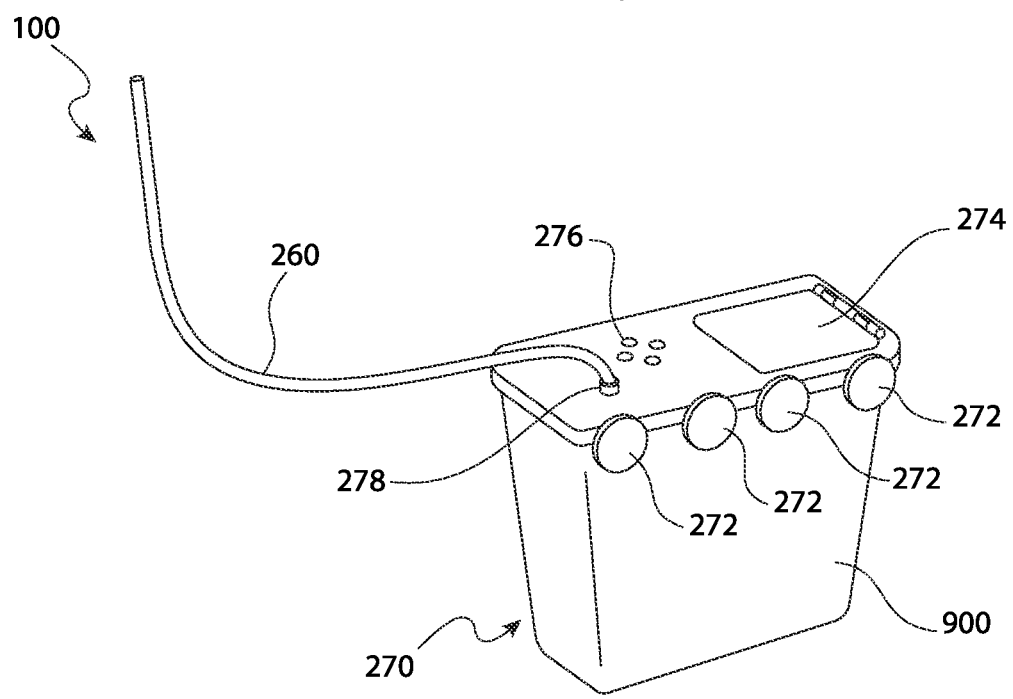
FIG. 8 is a rear isometric view of an automatic air conditioner drain system sanitizer, according to an embodiment of the present invention, illustrating the reservoir.
Figure 9A:
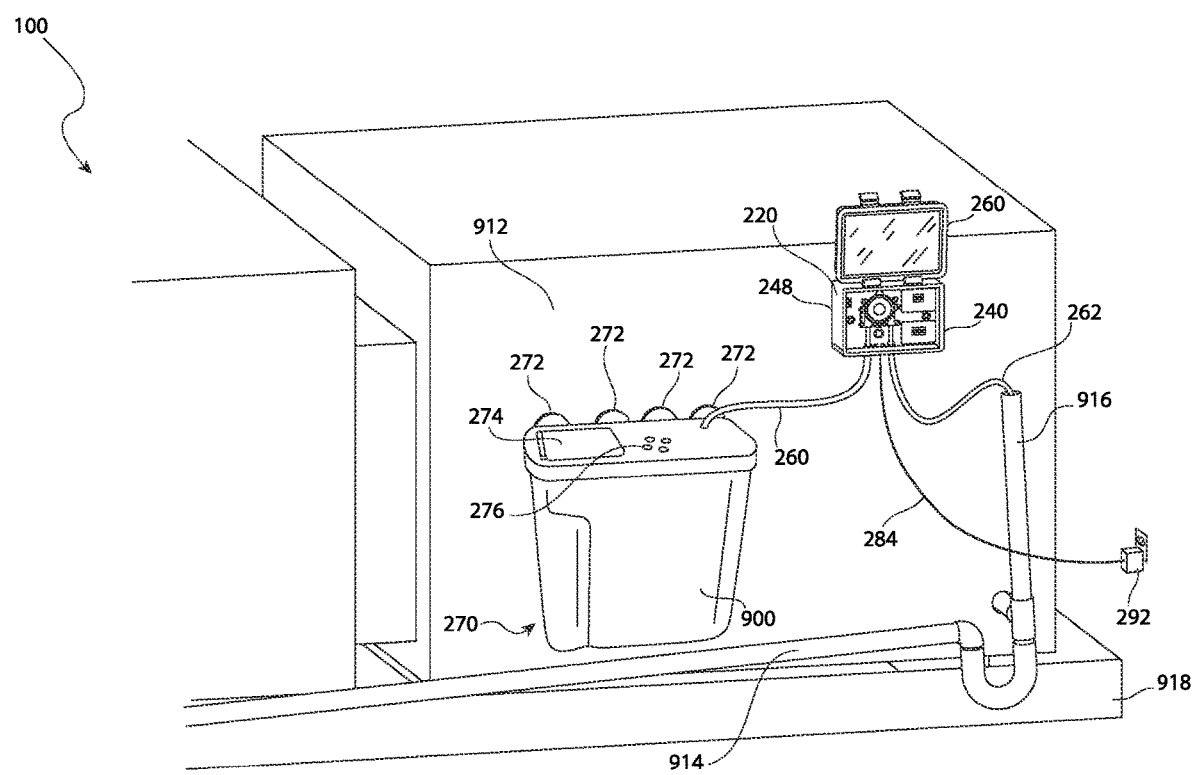
FIG. 9a is an in-use view of an automatic air conditioner drain system sanitizer, according to a method of use of the present invention.
Figure 9B:
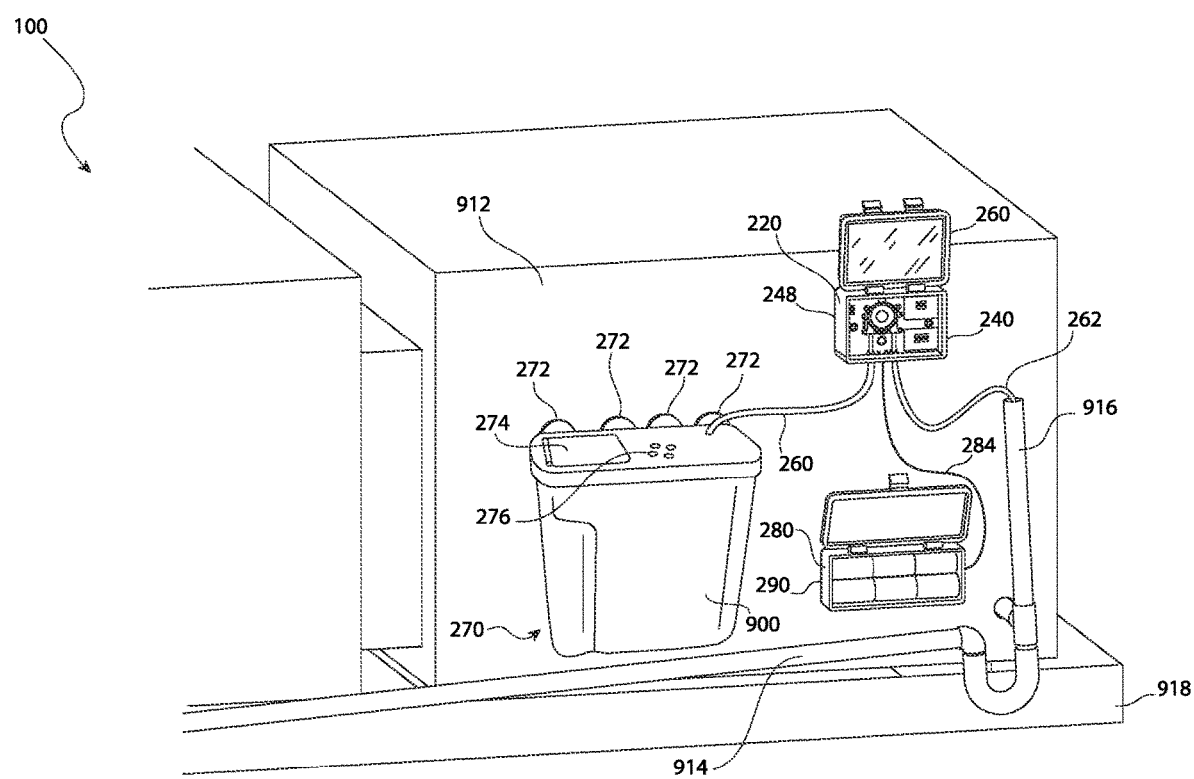
FIG. 9b is an in-use view of an automatic air conditioner drain system sanitizer, according to another method of use of the present invention.

The drain clearing solution 900 may be dispensed through the discharge tubing 262 into the drain line 914. The drain line 914 may be operable to drain condensation from an evaporator 912 but may be subject to blockage if the microorganisms block the drain line 914. Dispensing the drain clearing solution 900 into the drain line 914 may kill the microorganisms and prevent clogging. The specifics of how the discharge tubing 262 is coupled to the drain line 914 may vary from installation to installation. Non-limiting examples may comprise any or all of these options:

Routing the discharge tubing 262 directly into the drain line 914 via a drain line vent 916 tube as shown in FIG. 7.

Routing the discharge tubing 262 into the drain line 914 via a drain line access port that may be capped—including the option of replacing the access port cap with a different cap comprising an aperture for the discharge tubing 262.

Routing the discharge tubing 262 into the bottom of the evaporator 912 via an accessory drain port.

Routing the discharge tubing 262 into a drain pan 918 under the evaporator 912 which may also be fluidly coupled to the drain line 914.

In a preferred embodiment, the pump 200 may be a peristaltic pump. A peristaltic pump may be a type of positive displacement fluid transfer device for pumping a fluid using the rotary motion of a number of rollers within the pump 200 to force the fluid through a flexible tube.

The controller 220 may control the operation of the invention 100. The controller 220 may track time, may determine when to dispense the drain clearing solution 900, may energize the pump 200 by applying the pump activation signal to the pump 200, may control the quantity of the drain clearing solution 900 dispensed via the duration of the pump activation signal, and may deenergize the pump 200. It is envisioned that the controller 220 may be capable of wireless communication with a dedicated application for wireless control thereof.

The controller 220 may comprise a microcontroller 222. The microcontroller 222 may be a computer processor that incorporates the functions of a central processing unit in the form of one (1) or more integrated circuits. The microcontroller 222 may be a multipurpose, clock driven, register based, digital-integrated circuit. The microcontroller 222 may accept binary data as input, may process the binary data according to instructions stored in memory contained within the microcontroller 222, and may provide results as output. The microcontroller 222 may contain both combinational logic and sequential digital logic. The microcontroller 222 may operate on numbers and symbols represented in the binary number system.

The binary data comprising inputs and the results comprising outputs may relate to control signals received from and provided to other circuitry. As non-limiting examples, the microcontroller 222 may receive inputs from a timer 224 and may control outputs coupled to a motor drive circuit 230.

The timer 224 may count clock ticks in order to track elapsed time. As a non-limiting example, the timer 224 may track the passage of milliseconds and, by counting milliseconds, may be further operable to track the passage of seconds, minutes, hours, days, weeks, months, years, or any combination thereof. In some embodiments, the timer 224 may be operable to wake the microcontroller 222 from a sleep state on a periodic basis and/or after an elapsed time interval.

The controller 220 may comprise an input power conditioning circuit 226. The input power conditioning circuit 226 may condition power fed to the controller 220 and/or may monitor the power. As non-limiting examples, the input power conditioning circuit 226 may rectify the input power to prevent damage from reversed polarity, may filter the input power to prevent operational issues due to noisy power supplies, may limit the current draw from the power supply, may measure the voltage level of the input power, or any combination thereof.

In some embodiments, the controller 220 may comprise a supercapacitor 228 to power the microcontroller 222 during power interruptions.

The motor drive circuit 230 may convert one (1) or more digital outputs from the microcontroller 222 into the pump activation signal that may energize the pump 200.

A controller enclosure 240 may be a housing for the microcontroller 222, the pump 200, the timer 224, the motor drive circuit 230, and the input power conditioning circuit 226. The controller enclosure 240 may comprise a controller cover 246 that may be opened to access an operator interface 250. Preferably, the controller cover 246 is transparent. A DC power coupler 232, the intake tubing coupler 242, and the discharge tubing coupler 244 may be mounted on the controller enclosure 240 such that the DC power coupler 232, the intake tubing coupler 242, and the discharge tubing coupler 244 may be accessible outside of the controller enclosure 240.

The operator interface 250 may comprise a manual pump power control switch 252, a power level display 254, an interval selection control 256, and a dispense quantity control 258. The ON/OFF control 252 may energize and deenergize the controller 220. The power level display 254 may display the level of the power source. As a non-limiting example, when the controller 220 is being powered by a battery pack 280, the power level display 254 may indicate the remaining charge in the battery pack 280. The power control switch 252 can be used for initial priming of the invention 100 and for periodic testing of operation thereof. The interval selection control 256 may be adapted for a user to select the dispensing interval. The dispense quantity control 258 may be adapted for the user to select the quantity of the drain clearing solution 900 dispensed.

The solution reservoir 270 may store the drain clearing solution 900 prior to dispensing. As a non-limiting example, the solution reservoir 270 may be a container with a reservoir lid 274 enabling filling, a vent 276, and a solution reservoir tubing coupler 278. The intake tubing 260 may pass through the solution reservoir tubing coupler 278 on the reservoir 270 in order to reach the drain clearing solution 900.

The controller 220 may be powered from the power source. The power source may be a DC power adapter 292 that may plug into the DC power coupler 232 of the controller 220 if an AC outlet is available at the evaporator 912 of the air conditioning system. If an AC outlet is not available, the controller 220 may be powered from the battery pack 280. The battery pack 280 may comprise a plurality of batteries 282 in a battery enclosure 286 that may be mounted in proximity to the controller 220. The battery enclosure 286 may comprise a battery pack cover 288 that may be opened to replace the plurality of batteries 282. A DC power cable 284 from the battery pack 280 may be coupled to the DC power coupler 232 of the controller 220 to power the controller 220 from the battery pack 280.

In a preferred embodiment, the battery pack 280 may contain six (6) D cell batteries 282.

In some embodiments, at least one (1), but preferably a plurality of controller magnets 248 may be coupled to the rear of the controller enclosure 240, at least one (1) but preferably a plurality of battery pack magnets 290 may be coupled to the rear of the battery enclosure 286, and at least one (1) but preferably a plurality of solution reservoir magnets 272 may be coupled to the rear of the solution reservoir 270. The controller magnets 248, the battery pack magnets 290, and the solution reservoir magnets 272 may be operable to magnetically mount the controller enclosure 240, the battery enclosure 286, and the solution reservoir 270, respectively, on metal equipment such as the evaporator 912. In exemplary embodiments of the invention, the controller magnets 248 and the battery pack magnets 290 may be sixteen millimeters (16 mm) in diameter, and the solution reservoir magnets 272 may be thirty millimeters (30 mm) in diameter.

In use, the controller 220, the battery pack 280, and solution reservoir 270 may be mounted adjacent to the evaporator 912. As non-limiting examples, the controller 220, battery pack 280, and solution reservoir 270 may be mounted to the evaporator 912 using the controller magnets 248, battery pack magnets 290, and solution reservoir magnets 272, respectively. The DC power cable 284 from the battery pack 280 may be plugged into the DC power coupler 232 of the controller 220. The drain clearing solution 900 may be placed into the solution reservoir 270 and the solution reservoir 270 may be placed adjacent to the controller 220. One (1) end of the intake tubing 260 may be coupled to the intake tubing coupler 242 and the other end of the intake tubing 260 may be placed into the solution reservoir 270 via fluid communication with the solution reservoir tubing coupler 278. One (1) end of the discharge tubing 262 may be coupled to the discharge tubing coupler 244 and the other end of the discharge tubing 262 may be placed into the drain line 914. The user may select operational parameters such as the quantity to dispense and the dispensing interval using the operator interface 250 and may activate the controller 220. The controller 220 may periodically pump the drain clearing solution 900 from the solution reservoir 270 into the drain line 914 to prevent the growth of the microorganisms in the drain line 914.

During operation, the invention 100 enters a low power state for approximately nine seconds (9 s), then wakes up and reads the DIP switches looking for a settings change and activates the power level display 254 based on the voltage level of the battery pack 280. When the voltage level of the battery pack 280 reaches a value that the pump 200 can't be operated any longer the power level display 254 will flash every two seconds (2 s) signaling the batteries 282 must be changed. Such flashing is usually RED in color. If the system is running on AC power via the power adapter 292, the operation is identical and the power level display 254 will flash every ten seconds (10 s) as the power will always be "Full". Such flashing is usually GREEN in color.

The exact specifications, materials used, and method of use of the invention 100 may vary upon manufacturing. The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

The invention claimed is:

1. An automatic air conditioner drain system sanitizer, comprising:
    a pump moving a plurality of drain clearing solution from a pump inlet to a pump outlet;
    a solution reservoir containing the drain clearing solution, the solution reservoir includes a reservoir lid, a vent, and a solution reservoir tubing coupler, the pump draws the drain clearing solution into the pump from the solution reservoir;
    a controller having a controller enclosure housing for the controller, the pump, a timer, a motor drive circuit, and an input power conditioning circuit, the controller controls the pump and the solution reservoir; and
    an operator interface having a manual pump power control switch, a power level display, an interval selection control, and a dispense quantity control;
    wherein the pump draws the drain clearing solution into the pump from the solution reservoir through a plurality of intake tubing that is fluidly coupled to the pump inlet via an intake tubing coupler;
    wherein the pump discharges the drain clearing solution through a plurality of discharge tubing that is fluidly coupled to the pump outlet via a discharge tubing coupler;
    wherein the drain clearing solution is dispensed through the discharge tubing into a drain line;
    wherein the controller receives one or more inputs from the timer and controls one or more outputs coupled to the motor drive circuit;
    wherein the controller includes a plurality of controller magnets coupled to the rear of the controller enclosure, at least one battery pack magnets coupled to a rear of the battery enclosure, and at least one solution reservoir magnets coupled to a rear of the solution reservoir; and
    wherein a DC power coupler, the intake tubing coupler, and the discharge tubing coupler are mounted on the controller enclosure such that the DC power coupler, the intake tubing coupler, and the discharge tubing coupler is accessible outside of the controller enclosure.

2. The automatic air conditioner drain system sanitizer, according to claim 1, wherein the pump is an electromechanical pump.

3. The automatic air conditioner drain system sanitizer, according to claim 1, wherein the pump is a peristaltic pump.

4. The automatic air conditioner drain system sanitizer, according to claim 1, wherein the pump moves the drain clearing solution by applying a rotary motion, a reciprocating motion, a linear motion, or a combination thereof by one or more gears, one or more screws, one or more pistons, one or more rollers, one or more shuttle blocks, one or more vanes, one or more diaphragms, one or more plungers, one or more chains, one or more ropes, one or more impellers, or combinations thereof.

5. The automatic air conditioner drain system sanitizer, according to claim 1, wherein the drain line is operable to drain a plurality of condensation from an evaporator.

6. The automatic air conditioner drain system sanitizer, according to claim 1, wherein the drain clearing solution kills a plurality of microorganisms in the drain line to prevent clogging.

7. The automatic air conditioner drain system sanitizer, according to claim 1, wherein the discharge tubing is routed directly into the drain line via a drain line vent.

8. The automatic air conditioner drain system sanitizer, according to claim 1, wherein the discharge tubing is routed into the drain line via a drain line access port that is capped with a cap.

9. The automatic air conditioner drain system sanitizer, according to claim 8, wherein the cap is replaced with a different cap with an aperture to accommodate the discharge tubing.

10. The automatic air conditioner drain system sanitizer, according to claim 1, wherein the discharge tubing is routed into a bottom of an evaporator via an accessory drain port.

11. The automatic air conditioner drain system sanitizer, according to claim 1, wherein the discharge tubing is routed into a drain pan under the evaporator which is fluidly coupled to the drain line.

12. The automatic air conditioner drain system sanitizer, according to claim 1, wherein the controller is a microcontroller having a computer processor that includes a central processing unit having one or more integrated circuits that determines when to dispense the drain clearing solution, when to energize the pump, when to control the drain clearing solution dispensed, and when to deenergize the pump.

13. The automatic air conditioner drain system sanitizer, according to claim 1, wherein the timer counts a plurality of clock ticks in order to track elapsed time.

14. The automatic air conditioner drain system sanitizer, according to claim 1, wherein the controller includes a battery pack containing one or more batteries.

* * * * *